United States Patent [19]

Plotzker

[11] Patent Number: 4,515,761

[45] Date of Patent: May 7, 1985

[54] PROTECTIVE GARMENT OR COVER, COMPOSITE SEMIPERMEABLE BARRIER FABRIC, AND USE IN DETOXIFICATION

[75] Inventor: Irene G. Plotzker, Wilmington, Del.

[73] Assignee: E. I. Du Pont de Nemours and Company, Wilmington, Del.

[21] Appl. No.: 281,197

[22] Filed: Jul. 7, 1981

[51] Int. Cl.[3] ........................ A61L 9/00; B32B 27/28; C01B 7/00

[52] U.S. Cl. ........................................ 423/240; 55/16; 422/5; 423/245; 423/659; 428/422; 521/28

[58] Field of Search .............. 428/422; 521/28; 55/16; 210/690; 423/240, 245; 422/5

[56] References Cited

U.S. PATENT DOCUMENTS

| | | | |
|---|---|---|---|
| 3,034,928 | 5/1962 | Prichard | 117/143 |
| 3,068,125 | 12/1962 | Clayton et al. | 117/161 |
| 3,464,847 | 9/1969 | Megson et al. | 117/121 |
| 3,482,927 | 12/1969 | O'Brien et al. | 8/116.3 |
| 3,770,567 | 11/1973 | Grot | 161/189 |
| 3,784,399 | 1/1974 | Grot | 117/62.1 |
| 3,849,243 | 11/1974 | Grot | 161/189 |
| 3,884,885 | 5/1975 | Grot | 260/79.3 R |
| 3,969,285 | 7/1976 | Grot | 260/2.2 R |
| 4,085,071 | 4/1978 | Resnick et al. | 260/22 R |
| 4,194,041 | 3/1980 | Gore et al. | 428/422 X |
| 4,329,399 | 5/1982 | Swerlick | 428/422 |
| 4,356,318 | 10/1982 | Waller | 562/406 |

OTHER PUBLICATIONS

Chasanov and Epstein, J. Poly. Sci., vol. XXXI, pp. 399–414, (1958).
Epstein, Science, vol. 170, pp. 1396–1398, (1970).
Epstein and Mosher, J. Phys. Chem., vol. 72, pp. 622–625, (1968).
Courtney et al., JACS 79, pp. 3030–3036, (1957).
Augustinsson and Heimburger, Acta Chem. Scand., 9, 383-392, (1955).
Epstein and Rosenblatt, JACS 80, 3596–3598, (1958).
Gustafson and Martell, JACS 84, 2309–2316, (1962).
Larsson, Acta Chem. Scand. 12, 1226–1230, (1958).
Augustinsson, Acta Chem. Scand. 12, 1286–1291, (1958).
Casselman, Thompson and Bannard, Defense Research Establishment Ottawa Report No. DREO–R–810, Oct. 1979.
Zon, Report 1979, ARC/LS/TR–0060–2, ARCSL--CR–80002, AD–E410219.

*Primary Examiner*—Richard D. Lovering

[57] ABSTRACT

A protective garment fabricated at least in part from a composite fabric which contains a layer of a highly fluorinated ion exchange polymer having sulfonic acid multivalent metal ion salt functional groups.

20 Claims, No Drawings

PROTECTIVE GARMENT OR COVER, COMPOSITE SEMIPERMEABLE BARRIER FABRIC, AND USE IN DETOXIFICATION

The Government has rights in this invention pursuant to Contract DAAK 60-80-C-0092 awarded by U.S. Army Natick R&D Laboratories.

BACKGROUND OF THE INVENTION

Protective clothing of many types is now well-known for many and varied uses in protecting people from fire and harmful substances, such as suits for industrial workers, flame- and fire-resistant suits for firemen, forest fire fighters, race car drivers and airplane pilots, and suits for use by military personnel. Garments include not only complete, hermetic suits, but also individual garments such as trousers, jackets, gloves, boots, hats, head coverings, masks, etc.

Regulations restricting exposure to hazardous environments of various kinds, such as the Occupational Safety and Health Act, make it increasingly necessary to have better and more effective kinds of protective garments.

Such garments presently available are almost invariably of thick construction and heavy in weight, and are often fabricated at least in part from materials impermeable to water or water vapor, such as natural and synthetic rubbers and elastomers, chlorinated rubbers, etc. In the case of garments impermeable to water vapor, there is considerable discomfort to those wearing them, especially when the garments are of the hermetic variety, because of the entrapment of perspiration and body heat. Entrapment of heat and perspiration results in considerable discomfort of itself, and the heat stress which results from the prevention of loss of heat by the ordinary mechanism of evaporation of perspiration can rapidly reach a dangerous stage of heat prostration for the person wearing the garment.

It is an object of this invention to provide improved protective garments which possess the ability to permit the passage of water vapor through the fabric of the garment, and thereby provide improved comfort for the person wearing the garment.

It is another object of this invention to provide improved protective garments which possess not only the ability to permit the passage of water vapor through the fabric, but also the ability to act as a stable barrier to the passage of most organic substances, including toxic compounds, through the fabric. Such garments could protect those exposed to a wide variety of organic or harmful compounds.

It is a further object to provide such garments which are thin and light weight and which thus will more readily permit loss of heat by virtue of their light weight construction.

SUMMARY OF THE INVENTION

Briefly, the invention comprises using as a component of the fabric of a protective garment a layer of an ion exchange polymer, preferably a semipermeable fluorinated ion exchange polymer having sulfonic acid functional groups in the form of bi-, tri- or tetravalent metal salt. By "semipermeable" is meant permeable to water vapor but substantially impermeable to most organic substances.

More specifically, the present invention provides for the use in protective clothing of a composite fabric, said fabric containing as the essential component thereof a continuous film of a highly fluorinated ion exchange polymer having sulfonic acid metal ion salt functional groups, said metal ion having a valence of +2, +3 or +4, there being at least one fluorine atom attached to each carbon atom to which each said functional group is attached, said polymer having an equivalent weight no greater than about 2000.

There are also provided according to the invention a protective garment and a waterproof protective cover fabricated at least in part from the composite fabric described in the previous paragraph.

There is further provided according to the invention a process wherein (a) water permeates from a first space adjacent a first side of a barrier to a second space adjacent the second side of said barrier, said barrier having as the essential component thereof a continuous film of a highly fluorinated ion exchange polymer having sulfonic acid metal ion salt functional groups, said metal ion having a valence of +2, +3 or +4, there being at least one fluorine atom attached to each carbon atom to which each said sulfonic acid group is attached, said polymer having an equivalent weight no greater than about 2000, and (b) a hazardous substance, said substance being a toxic organophosphorus compound having a

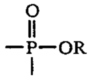

moiety wherein R is a $C_1$ to $C_{10}$ alkyl group, or a blistering agent which contains two or more chloroethyl groups, present in said second space (i) permeates only slowly into said barrier and (ii) that portion of said hazardous substance which permeates into said barrier is detoxified at least in part by said polymer, whereby the rate of penetration of said hazardous substance into said first space is substantially decreased.

DETAILED DESCRIPTION OF THE INVENTION

The composite fabric from which protective garments of the invention are made contains as the essential component thereof a continuous film or layer of a highly fluorinated ion exchange polymer having sulfonic acid functional groups in the form of multivalent metal salt as set forth below, there being at least one and preferably two fluorine atoms attached to the carbon atom to which the sulfonic group is attached. By "highly fluorinated" is meant that the polymer in ion exchange form has at least as many C—F groups as it has C—H groups.

The highly fluorinated ion exchange polymers can be copolymers of fluorinated monomers containing the sulfonic functional group with nonfunctional monomers such as tetrafluoroethylene, trifluoroethylene, vinylidene fluoride, chlorotrifluoroethylene, etc. The polymers are preferably perfluorinated polymers prepared from perfluoro sulfonic monomers and tetrafluoroethylene. Such polymers and their preparation are now well-known in the art, and are described, e.g., in U.S. Pat. No. 3,282,875. Such polymers are unaffected by a large variety of chemicals including typical decontamination systems used after exposure of a protective garment to various toxic and harmful chemicals. Perfluorinated polymers of this type have retained good physical properties after exposure to chlorine gas and strong hot caustic solution within an operating chloralkali cell for times in excess of two years.

In accordance with the present invention, for use as a component of a fabric used in a protective garment or cover, the highly fluorinated ion exchange polymer should be in the form of a multivalent metal ion salt thereof, in particular, a metal ion salt having a valence of +2, +3 or +4. Examples of suitable metal ions include $Ca^{+2}$, $Mg^{+2}$, $Al^{+3}$, $Zn^{+2}$, $Ce^{+3}$, $Ce^{+4}$, $Cr^{+3}$, $Ni^{30}$ 2 and $Co^{+2}$. Use of ion exchange polymer in such multivalent metal ion salt form is advantageous over use of polymer in the form of the free sulfonic acid or $Na^{+}$ or $K^{+}$ salt thereof, because the multivalent metal salt form provides improved selectivity of transport rate of water versus toxic organic compounds. More specifically, the multivalent metal salts provide better barrier properties against toxic organic compounds. Although in some cases the water transport rate of the multivalent metal salts is also lower than that of the $Na^{+}$ or $K^{+}$ forms, in other cases the water transport rate is comparable to that of the $Na^{+}$ or $K^{+}$ forms. Thus, $Ca^{+2}$ is a highly preferred metal ion species, as it has a lower transport rate for organic compounds, and a comparable transport rate for water, when compared with the $Na^{+}$ and $K^{+}$ forms.

The multivalent metal ion salt forms of the highly fluorinated ion exchange polymer are suitably and conveniently made by ion exchange from the $H^{+}$, $Na^{+}$ or $K^{+}$ forms with an aqueous solution containing the desired multivalent ion; aqueous solutions of any convenient compound, such as a hydroxide, chloride, nitrate, sulfate, etc., are suitable. Immersion in the solution containing the multivalent metal ion for 2 hours or more is suitable, and 16 to 24 hours is generally ample.

The polymers, films, etc., referred to herein in multivalent metal ion salt form have at least about 80 mol % of the sulfonate groups of the polymer in the multivalent metal ion salt form, and generally at least about 90 mol % of the sulfonate groups in such form. The remainder of the groups, if any, are usually in the form employed in the preparative ion exchange procedure, generally the $H^{+}$, $Na^{+}$ or $K^{+}$ form.

So as to have a high moisture permeability which will provide a garment having comfortable wearing properties, the highly fluorinated ion exchange polymer should have an equivalent weight of no greater than about 2000, preferably no greater than about 1500. (The equivalent weight of such a polymer is the number of grams of polymer which, when in $H^{+}$ form, provides one mol of hydrogen ion.) Equivalent weights as low as 1100 and even 1000 provide exceptionally high water vapor transmission rates. The water vapor transmission rates of fabrics containing a layer of such polymer is sufficiently high to permit the loss by permeation of enough perspiration so that a person wearing the garment is substantially more comfortable than he would be if wearing an impermeable garment. However, with increase in equivalent weight, the suppleness of the highly fluorinated ion exchange polymer increases, such polymer is more easily extruded in thinner films, and mechanical properties such as flex life improve; such factors can be considered when selecting the equivalent weight of the polymer to be used in any particular composite fabric.

The thickness of the layer of highly fluorinated ion exchange polymer is not critical to the permeation rate of water vapor, which is so high that it is almost independent of the thickness of the film in the range of thickness dealt with herein. In some cases where a garment is to protect the wearer from exposure to a harmful compound, extremely thin layers of the highly fluorinated ion exchange polymer may not be suitable. In those cases where the composite fabric is made by lamination of one or more component fabrics with a preformed film of the highly fluorinated ion exchange polymer or a precursor polymer thereof, the thickness of the film used is generally in the range of about 10 to 125 micrometers (about 0.4 to 5 mils), preferably about 10 to 50 micrometers. In those cases where one step in preparation of the composite fabric is coating a component fabric with a solution of the highly fluorinated ion exchange polymer or a precursor thereof followed by removal of the solvent by drying, composite fabrics containing a thinner layer of highly fluorinated ion exchange polymer, down to about 2.5 micrometers (0.1 mil) thick, and even down to about 1 micrometer (0.04 mil) thick, can be made. For garments intended for protecting the wearer from exposure to a harmful substance, the layer of highly fluorinated ion exchange polymer should be continuous, i.e., it should be substantially free of pinholes, so as to prevent leakage of organic substances to within the garment. A layer of highly fluorinated ion exchange polymer about 12 to 50 micrometers (0.5–2 mil) thick is most preferred.

The highly fluorinated ion exchange polymer should be of high enough molecular weight to be film forming and to have adequate toughness to survive conditions of wear without developing leaks which would destroy its integrity, and can be, e.g., linear or branched.

The component fabrics used in making the composite fabric are many and varied in type. They can be, but are not limited to, cotton, rayon, wool, silk, linen, polyester such as polyethylene terephthalate, polyamides such as polyhexamethylene adipamide, polyhexamethylene decanedicarboxamide, polyhexamethylene dodecanedicarboxamide, polyepsilon-caproamide or the polyamide of bis-para-aminocyclohexylmethane and dodecanedicarboxylic acid, aramids such as poly-meta-phenylene isophthalamide or poly-para-phenylene terephthalamide, polyolefins such as polyethylene, polypropylene or polytetrafluoroethylene, acrylics such as polyacrylonitrile, polybenzimidazoles, polyarylene sulfides, polyarylene-imide-amides, polyphenol-formaldehyde, polyimides, glass, flame-retardant cotton, etc., and blends of two or more of the foregoing. Carbonized cotton, acrylic, etc., fiber or fabric, or other adsorptive materials in any form such as activated carbon, can also be included as components of the composite fabrics. A component fabric can be woven, including, e.g., plain and ripstop weaves, knitted, nonwoven, felted, spunbonded, or poromeric fabric, or a fibrillated film, or a film or extrudate made or treated by any means to make it porous or microporous. In the case of such microporous component, those having a pore size of at least about 0.5 micrometer are preferred. Activated carbon or other adsorptive substances can be incorporated in the composite fabric by distributing it in a thin foamed layer included as one component of the composite fabric, or in any one layer or between two layers of said ion exchange polymer, or in any other suitable manner.

It is preferred, but not essential, that all of the components of the composite fabric of the invention, whether they be fabrics or continuous films, should be hydrophilic in nature. The term "hydrophilic", when used in reference to a film, means that such film will transfer substantial amounts of water through the film by absorbing water on one side where the water vapor concentration is high, and desorbing or evaporating it on the opposite side where the water vapor concentration is low. The term "hydrophilic", when used in reference to a fabric, means that water will spread on the fabric and wick into its porous structure. In the case of those component fabrics listed in the previous paragraph which are not hydrophilic, such as microporous polytetrafluoroethylene fabric, they can, if desired, be impregnated throughout the structure and on both surfaces with sufficient hydrophilic polymer to render them, in effect, reinforced hydrophilic films; non-hydrophilic materials when so impregnated and coated lose their non-hydrophilic character and behave as hydrophilic components. Films of the highly fluorinated ion exchange polymers referred to hereinabove are hydrophilic, and such polymers are suitable for rendering hydrophilic those component fabrics which would otherwise be non-hydrophilic.

The composite fabric can take any of manifold forms. In addition to the layer of highly fluorinated ion exchange polymer, the composite fabric further comprises at least one layer of component fabric, preferably at least two layers of component fabric which may be the same or different. When the composite fabric contains at least two layers of component fabric, preferably there will be at least one layer of component fabric on each side of the layer of ion exchange polymer so as to provide protection to the latter from mechanical damage. It is further preferred to use as one of the outermost component fabrics a layer of a flame-resistant and/or wear-resistant fabric, and to fabricate the garment with such component fabric being on the outside of the garment.

A preferred embodiment of the composite fabric is that made from only one layer of component fabric in addition to the layer of highly fluorinated ion exchange polymer. Such composite fabric is intended to be used in a protective garment with the layer of highly fluorinated ion exchange polymer on the outside of the garment, and the component fabric side of the composite fabric on the inside of the garment; this orientation of the composite fabric presents a smooth, non-porous, barrier surface against a cloud of toxic gas or liquid droplets, and thereby does not absorb or trap any of the toxic substance in pores or interstices of the composite fabric, thus permitting easy decontamination after exposure to the toxic substance. Garments which are fabricated with a porous or microporous surface toward the outside, once contaminated by entrapment of a toxic substance in the pores, are at least extremely difficult, and often impossible, to decontaminate, and when decontamination is impossible must be carefully disposed of after but a single use. Those protective garments of the invention which do not contain a microporous layer are easily decontaminated, and thus provide for multiple reuse of the garment. With the indicated orientation of the composite fabric, there is the further advantage that the inner layer of hydrophilic component fabric soaks up perspiration and brings it into direct contact with the outer layer of moisture-transporting ion exchange polymer. Accordingly, such a composite fabric is a preferred fabric, in that it possesses advantages over fabrics which contain a hydrophobic microporous layer as a component thereof.

It should be noted that there are some situations in which an exposed outer layer of highly fluorinated ion exchange polymer could be damaged, in which case the loss of integrity of the barrier layer of the garment would endanger the person wearing the garment; in those situations, it is advisable that a wear-resistant outergarment be worn over the protective garment to aid in precluding damage to the latter. Such overgarments, following contamination, can either be laundered for reuse, or be of inexpensive, light-weight construction adapted for discarding after exposure to a toxic substance.

The composite fabric can be made from the component fabrics and either a film of highly fluorinated ion exchange polymer or a fabric either melt- or solution-coated with a continuous layer of highly fluorinated ion exchange polymer. The composite fabric is made in some cases by the use of heat and either vacuum or pressure, and in other cases by using suitable adhesives or meltable or soluble polymers to adhere the several components together. In some cases, the highly fluorinated ion exchange polymer is maintained in the form of a melt-fabricable precursor, e.g., with functional groups such as $—SO_2F$, during formation of the composite fabric, and after the composite fabric has been made the melt-fabricable precursor is hydrolyzed and converted to the metal salt form defined above. In those cases where a precursor of a highly fluorinated ion exchange polymer having functional groups such as $—SO_2F$ groups is used in combination with a component fabric of polyolefin or polyfluorinated polyolefin, hydrolysis can be under any suitable conditions such as those used with hydrolysis bath A in the examples below, but when such a polymer is used in combination with a component fabric of a nylon, cotton, wool or other polymer which may be damaged by vigorous hydrolysis conditions, hydrolysis after fabrication of composite fabric prepared therefrom should be under milder conditions such as with ammonium hydroxide. The polymer can alternatively be put into the form of the sulfonic acid or an alkali metal, ammonium or amine salt thereof (preferred amines include p-toluidine and triethanolamine) before forming a composite fabric therefrom, and in such cases the composite fabric can be prepared by using a small amount of a highly fluorinated ion exchange polymer having, e.g., $—COOCH_3$ functional groups as an adhesive bonding agent, which can be hydrolyzed under mild conditions, or by using other types of adhesive such as ethylene/vinyl acetate based hot melt adhesives or two-component epoxy adhesives. Composite fabrics made without an adhesive bonding agent are preferred, inasmuch as most bonding agents interfere with passage of water through the composite fabric, and to the extent used, reduce the active area through which water permeates. If such an adhesive bonding agent is used, a highly fluorinated ion exchange polymer having, e.g., $—COOCH_3$ functional groups is preferred, as it can be hydrolyzed to alkali metal carboxylate form, which has a high permeability to water; such polymers are known in the art, e.g., in Belgian Pat. No. 866,121. The various salt forms of a functional group can freely be interconverted from one to another, and to or from the free acid form, in either a component material or a composite fabric, as desired, by treatment with a solution containing the cation of the desired form. The composite fabric can be made from the components in some cases in a single operation, and in other cases by a series of sequential steps.

The composite fabrics described above can be used in fabrication of protective garments by techniques known in the art, including sealing of seams and joints by use of radio frequency heating or other known electronic bonding techniques, or by heat and pressure, in some cases with the aid of adhesives or sealants at the seams and joints to prevent leaks at those points. Garments can also be made by sewing, but in cases where a leak-free construction is desired the sewn seams should also contain a sealant or adhesive.

The composite fabrics and garments made therefrom are highly permeable to water vapor. Accordingly, a person wearing such a garment does not suffer heat stress which results from interruption of the usual mechanism of loss of body heat by evaporation of the water of perspiration, and discomfort from the retention of the water of perspiration within the garment is reduced. While the composite fabrics are also permeable to a few low molecular weight organic compounds such as methanol and ethanol, and while the permeation rate for an organic compound depends on the type of compound and its molecular weight, the permeation rates for most organic compounds are extremely low and in the case of many organic compounds the composite fabric is substantially impermeable to the compound. It is believed that the composite fabrics described herein possess barrier properties against a variety of hazardous substances, poisonous compounds, blistering agents, lachrymators, and irritants. As will be seen, the composite fabrics permit the passage of large amounts of water vapor.

The protective garment of this invention is believed to have the ability to protect the wearer against hazardous substances, such as certain toxic organophosphorous compounds that are anticholinesterases, which compounds have the common feature that they contain a

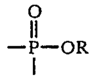

moiety where R is a $C_1$ to $C_{10}$ alkyl group, and halogenated organic sulfides and amines such as the blistering agents which contain two or more chloroethyl groups, e.g., compounds of the formula $(ClCH_2CH_2)_2Z$, where Z is S or NQ, and Q is $CH_3$—, $C_2H_5$— or $ClCH_2CH_2$—. It has been found that the perfluorinated sulfonate polymer when in the form of the calcium or magnesium salt has a lower tranport rate for dimethyl methylphosphonate than the same polymer in the hydrogen form or sodium or potassium salt form, and it is thus believed that garments made of fabric containing a layer of such polymer in the calcium, magnesium, or other multivalent salt form will provide better protection against other phosphonates such as anticholinesterases, and against other hazardous substances, than garments made of fabric containing a layer of such polymer in hydrogen, sodium or potassium form. The essential component of the composite fabric used in making the protective garment, a highly fluorinated polymer having multivalent metal ion sulfonate functional groups and at least one fluorine atom attached to each carbon atom to which each such group is attached, is believed to be capable in many cases of complexing with and/or detoxifying such organic substances. The ability of the highly fluorinated ion exchange polymer to act as a barrier to such organic substances, and additionally to complex with and/or detoxify at least in part that portion which permeates into the barrier, thus substantially retards the rate of penetration of such organic substances into the space within a protective garment of the invention.

The composite fabrics have good mechanical properties, such as toughness, strength and flex life. Both the composite fabrics and garments fabricated from them have good storage stability, such that the garments can be retained for long periods before actual use of them.

To further illustrate the innovative aspects of the present invention, the following examples are provided.

In the examples, water transport rates were measured using an inverted cup technique similar to that of ASTM (American Society for Testing Materials) method E 96-66. Transport rates of substances other than water were measured by a similar technique, except at a different relative humidity as specified. The weight of the cup and its contents was plotted vs. time, and the line which best fit the linear portion of the curve was drawn; the magnitude of the slope of the line was taken as the mass transfer rate.

In Examples 9, 10, K, L and M, apparatus for continuous preparation of composite fabric was employed which comprised a hollow roll with an internal heater and an internal vacuum source. The hollow roll contained a series of circumferential slots on its surface which allowed the internal vacuum source to draw component materials in the direction of the hollow roll. A curved stationary plate with a radiant heater faced the top surface of the hollow roll with a spacing of about 6 mm (¼ inch) between their two surfaces.

During a lamination run, porous release paper was used in contacting the hollow roll as a support material to prevent adherence of any component material to the roll surface and to allow vacuum to pull component materials in the direction of the hollow roll. Feed and takeoff means were provided for the component materials and product. In the feed means one idler roll of smaller diameter than the hollow roll was provided for release paper and component materials. The feed and takeoff means were positioned to allow component materials to pass around the hollow roll over a length of about 5/6 of its circumference. A further idler roll was provided for the release paper allowing its separation from the other materials. Takeoff means were provided for the release paper and a composite fabric.

EXAMPLES

Examples 1 and 2, and Comparative Examples A, B and C

A film of a copolymer of tetrafluoroethylene (herein referred to as TFE) and perfluoro(3,6-dioxa-4-methyl-7-octenesulfonyl fluoride) (herein referred to as PSEPVE), having an equivalent weight of 1200 and a thickness of 0.13 mm (5 mils) was hydrolyzed to —$SO_3K$ form with a hydrolysis bath consisting of 15% by wt. of potassium hydroxide, 25% by wt. of dimethylsulfoxide and 60% by wt. of water (herein referred to as hydrolysis bath A), and converted to —$SO_3H$ form by washing with aqueous nitric acid. A piece of this film was retained (Comp. Ex. A). Other pieces of the film were separately converted to salts of various metal ions by immersion for ca. 16 hours in aqueous solutions of NaOH (20 g/l), KOH (30 g/l), $CaCl_2$ (29 g of $CaCl_2.2H_2O$/l), and $MgCl_2$(40 g of $MgCl_2.6H_2O$/l). Rates of transport of dimethyl methylphosphonate (herein referred to as DMMP), $CH_3PO(OCH_3)_2$, a chemical compound employed as a simulant of anticholinesterases, were measured. The results are summarized in Table I.

TABLE I

| Ex. | Metal Ion | Conditions | DMMP wt. loss in 6 h (g) | DMMP transport rate ($g/m^2 \cdot 24$ h) |
|---|---|---|---|---|
| 1 | $Ca^{+2}$ | 24° C., 22% RH | 0.0192 | 17.5 |
| 2 | $Mg^{+2}$ | 23.5° C., 25.3% RH | 0.0310 | 25.5 |
| A | $H^{+}$ | 24° C., 22% RH | 2.6833 | 3450 |
| B | $Na^{+}$ | 24° C., 22% RH | 2.6500 | 3750 |
| C | $K^{+}$ | 24° C., 22% RH | 0.8772 | 1650 |

Examples 3 and 4, and Comparative Example D

Pieces of a film of TFE/PSEPVE copolymer having an equivalent weight of 1350 and a thickness of 0.13 mm were hydrolyzed and separately converted to salts of various metal ions as described in the first group of examples. Transport rates for DMMP were measured, and are summarized in Table II.

TABLE II

| Ex. | Metal Ion | Conditions | DMMP wt. loss in 6 h (g) | DMMP transport rate ($g/m^2 \cdot 24$ h) |
|---|---|---|---|---|
| 3 | $Ca^{+2}$ | 22° C., 21.6% RH | 0.0424 | 18.5 |
| 4 | $Mg^{+2}$ | 24° C., 32% RH | 0.0064 | 6.1 |
| D | $Na^{+}$ | 23° C., 23.4% RH | 1.2365 | 1720 |

Examples 5 and 6, and Comparative Examples E and F

Pieces of a film of TFE/PSEPVE copolymer having an equivalent weight of 1350 and a thickness of 0.05 mm (2 mils) were hydrolyzed and separately converted to salts of metal ions as described in the first groups of examples. Transport rates for water were measured, and are summarized in Table III.

TABLE III

| Ex. | Metal Ion | Conditions | Water transport rate ($g/m^2 \cdot 24$ h) |
|---|---|---|---|
| 5 | $Ca^{+2}$ | 25° C., 30% RH | 14,700 |
| 6 | $Mg^{+}$ | 25° C., 30% RH | 14,800 |
| E | $H^{+}$ | 25° C., 30% RH | 23,500 |
| F | $Na^{+}$ | 25° C., 30% RH | 12,100 |

Examples 7 and 8, and Comparative Examples G, H and J

In order to ascertain the effect of water on DMMP transport, experiments were carried out using a cell in which the film to be tested was in contact with DMMP on one side (top) and distilled water on the other (bottom). The upper compartment of the cell was closed with a loose fitting glass cover, and the lower compartment was equipped with a small port, so that samples could be periodically removed from each compartment for analysis by gas chromatography. The film sample was clamped between the two compartments with a neoprene gasket on each side of the film to be tested. The exposed area of film in the test was circular, 7.62 cm (3 in) in diameter. The bottom compartment was filled with water (ca. 185 ml), so that it would contact the lower surface of the film, and the water was stirred by a magnetically-impelled stirring bar. In the top compartment was placed 50 ml of DMMP. Additional samples of film like those of Exs. 1 and 2 and Comp. Exs. A, B and C were thus tested over a period of 6–6.5 hours.

For each time of analysis, the number of grams of DMMP that had passed through the membrane into the water compartment was calculated by using the equations:

$$\frac{100D}{D + (W_W - H)} = B \text{ and } \frac{100\,(W_D - D)}{(W_D - D) + H} = T,$$

where B is the weight percent DMMP in the bottom (water) compartment, T is the weight percent DMMP in the top compartment, $W_D$ is the original weight of DMMP in the top compartment (here, 56.3 grams), $W_W$ is the original weight of distilled water (here, 185 grams), D is the number of grams of DMMP that have diffused into the bottom compartment, and H is the number of grams of water that have passed through the membrane into the DMMP compartment. In this determination, the amount of water and DMMP in the film was ignored, as there is no easy way to determine those amounts. These simultaneous equations were solved for D and H. D was plotted against time of measurement (hours), and a mass transfer rate was calculated by finding the slope of the best-fit line for the linear portion of the curve, multiplying by 24 and dividing by the exposed film area ($45.60 \times 10^{-4} m^2$). The results are summarized in Table IV.

TABLE IV

| Ex. | Metal Ion | Transport Rate ($g/m^2 \cdot 24$ h) DMMP into water | Water into DMMP |
|---|---|---|---|
| 7 | $Ca^{+2}$ | 4950 | 5930 |
| 8 | $Mg^{+2}$ | 17100 | 10400 |
| G | $H^{+}$ | 14200* | 42900 |
| H | $Na^{+}$ | 17000 | 15000 |
| J | $K^{+}$ | 18000 | 30700 |

*Rate was significantly nonlinear; average rate was 19600.

The test described in this set of examples is a very severe test, and embodies conditions not necessarily encountered during actual use. In any case, it is noted that the $Ca^{+2}$ form of the polymer exhibited significantly lower transport rate of DMMP than the other forms tested.

Examples 9 and 10, and Comparative Examples K, L and M

Using apparatus as described hereinabove, a composite fabric was made by heat laminating a film of TFE/PSEPVE copolymer, having an equivalent weight of 1350 and a thickness of 0.036 mm (1.4 mils), that had been hydrolyzed on only one surface to a depth of 0.015 mm, and a component woven fabric of a blend of 95% poly-meta-phenylene isophthalamide fibers and 5% poly-para-phenylene terephthalamide fibers, said fabric having a basis weight of 150 $g/m^2$; lamination was carried out with the component fabric against the release paper, and the unhydrolyzed side of the film against the component fabric. The radiant heater on the curved plate was at 360° C., the hollow roll was at 240° C. and was operated at a vacuum of $7.1 \times 10^4$ pascals (21 inches of mercury), and the line speed was 0.3 m/min (1 ft/min). The product was immersed for 48 hours in a 1:1 volume mixture of conc. ammonium hydroxide and methanol to hydrolyze $—SO_2F$ groups, rinsed with water, immersed for 5 hours in a 2.85% by wt. aqueous solution of sodium chloride to ion-exchange the functional groups to —$SO_3Na$ form, again rinsed with water, and dried, to provide a composite fabric in $Na^+$ form. Portions of the composite fabric in $Na^+$ form were separately immersed in aqueous 2 N hydrochloric acid for 5.5 hrs to provide fabric in $H^+$ form, and in aqueous potassium hydroxide solution (30 g KOH/l) for ca. 16 hrs to provide fabric in $K^+$ form. A portion of the composite fabric in $Na^+$ form was immersed for 19 hours in a 5.48% by wt. aqueous solution of $CaCl_2.2H_2O$ to ion-exchange $Na^+$ for $Ca^{+2}$; analysis by atomic absorption of the extracted metal ions indicated that the composite fabric contained 0.33% by wt. $Ca^{++}$ and 230 ppm (wt.) $Na^+$, and that in a minimum of 94 mol % of the sulfonate groups, sodium had been replaced by calcium. Another portion of the composite fabric in $Na^+$ form was immersed for 19 hrs in a 7.41% by wt. aqueous solution of $MgCl_2.6H_2O$ to exchange $Na^+$ for $Mg^{++}$; analysis indicated that the composite fabric contained 0.29% by wt. $Mg^{++}$ and 240 ppm (wt.) $Na^+$, and that in a minimum of 95 mol % of the sulfonate groups, sodium had been replaced by magnesium.

Transport rates for DMMP and water were measured using test cells having two compartments and a port in each compartment for use in removing samples for analysis. The exposed area of composite fabric in the test cell was 20.27 $cm^2$. Test samples were checked for leaks after mounting in a test cell by attaching a water-containing bubbler to the top compartment, and raising the air pressure slightly in the bottom compartment; if bubbles appeared the sample was rejected. In the compartment adjacent the component fabric side of the composite fabric was placed 30 ml of distilled water, and in the compartment adjacent the component film side of the composite fabric was placed 13.5 g of DMMP. The ports were closed with rubber caps, and the cell was mounted on a shaker to assure that adequate mixing occurred in each compartment. Samples removed periodically from each compartment were analyzed by gas chromatography. The amounts of water and DMMP transported were calculated with the formula as described in the previous set of examples, using $W_W=30$ g and $W_D=13.5$ g. Transport rates were then calculated, using $20.27\times10^{-4}m^2$ as the exposed area. The results are summarized in Table V.

TABLE V

| Ex. | Metal Ion | Test Duration (hours) | DMMP transported (g) | DMMP transport rate (g/m² · 24 h) | Water transported (g) | Water transport rate (g/m² · 24 h) |
|---|---|---|---|---|---|---|
| 9 | $Ca^+$ | 6.5 | 1.54 | 2800 | 5.60 | 7430 |
| | | 6.5 | 1.49 | 2730 | 5.47 | 6960 |
| 10 | $Mg^{+2}$ | 6.5 | 3.49 | 6070 | 6.87 | 9010 |
| | | 6 | 2.75 | 5200 | 5.49 | 9110 |
| | | 6 | 2.03 | 4410 | 7.91 | 12000 |
| K | $K^+$ | 6.5 | 2.41 | 4350 | 7.97 | 9320 |
| | | 6 | 2.61 | 4990 | 7.54 | 12600 |
| | | 6 | 3.25 | 6310 | 3.95 | 5830 |
| L | $Na^+$ | 4.5 | 3.53 | 6820 | 6.16 | 13100 |
| | | 6 | 2.32 | 6750 | 15.5 | 30900 |
| M | $H^+$ | 2 | 2.14 | 11800 | 4.64 | 58900 |
| | | 3.5 | 4.03 | 8970 | 8.33 | 24700 |
| | | 6 | 6.12 | 11400 | 4.56 | 5470 |

Examples 11-20 and Comparative Examples N, P and Q

Additional pieces of the film in —$SO_3H$ form of Exs. 1-2 were separately converted to salts of various other metal ions by immersion in aqueous solutions of $Al(NO_3)_3$ (100.0 g of $Al(NO_3)_3.9H_2O$/l), $BaCl_2$ (97.8 g of $BaCl_2.2H_2O$/l), $Ce(NO_3)_3$ (77.2 g of $Ce(NO_3)_3.6H_2O$/l, not all dissolved), $CoCl_2$(95.2 g of $CoCl_2.6H_2O$/l), $CrCl_3$(71.0 g of $CrCl_3.6H_2O$/l), $NiSO_4$(105.2 g of $NiSO_4.6H_2O$/l), $ZnCl_2$(45.3 g of $ZnCl_2$/l), and $Ce(NO_3)_4$ (aqueous solution 0.5 N in $Ce(NO_3)_4$ and 2 N in $HNO_3$). Rates of transport of DMMP and water were measured, and the results are summarized in Table VI. The results for water are expressed as water vapor permeabilities (averages of two to four runs measured at different relative humidities) inasmuch as they incorporate into the numerical values reported the relative humidity (RH). The water vapor permeability P is obtained from the water transport rate R (in g/cm².h) with the formula $$P = \frac{R \cdot t}{V}$$

where t is the sample thickness (cm) and V is the difference in vapor pressure of water on the two sides of the sample, which is determined by the formula $$V=(1-RH)(V_t)$$

where RH is the relative humidity expressed as a decimal, and $V_t$ is the vapor pressure of water at the temperature of the experiment, expressed in torr.

TABLE VI

| Ex. | Metal Ion | DMMP transport rate* (g/m² · 24 h) | Water vapor permeability (g · cm/cm² · h. torr) |
|---|---|---|---|
| 11 | $Al^{+3}$ | 10.6* | $3.26 \times 10^{-5}$ |
| 12 | $Ba^{+2}$ | 34.4 | $2.24 \times 10^{-5}$ |
| 13 | $Ce^{+3}$ | 14.4 | $2.96 \times 10^{-5}$ |
| 14 | $Co^{+2}$ | 5.99 | $4.67 \times 10^{-5}$ |
| 15 | $Cr^{+3}$ | 568 | $3.66 \times 10^{-5}$ |
| 16 | $Ni^{+2}$ | 80.6 | $4.44 \times 10^{-5}$ |
| 17 | $Zn^{+2}$ | 472 | $4.65 \times 10^{-5}$ |
| 18 | $Ce^{+4}$ | 336* | $3.06 \times 10^{-5}$ |
| 19 | $Ca^{+2}$ | 20.0 | $4.18 \times 10^{-5}$ |
| 20 | $Mg^{+2}$ | 25.5 | $4.83 \times 10^{-5}$ |
| N | $Na^+$ | 3920 | $4.31 \times 10^{-5}$ |
| P | $H^+$ | 3240 | $6.46 \times 10^{-5}$ |
| Q | $K^+$ | 1650 | |

*Averages of 2 to 4 values (single value in Ex. 16) measured at 21.5 to 28° C. and 14 to 30% RH. The rate is over a 5- to 6.5-hour period, except for Ex. 11, which is over a 1- to 2-hour period, after which there was a net gain in weight, apparently due to uncontrolled high humidity. For Ex. 18, a transport rate of 1200 in one run is presumed to be incorrect due to leak in film.

Examples 21 and 22 and Comparative Examples R, S and T

Additional pieces of the films of Exs. 1 and 2 and Comparative Exs. A, B and C were used to test the rate of transport of beta-chlorodiethyl sulfide (herein referred to as CDES), a chemical compound employed as a simulant of bis-beta-chloroethyl sulfide. Transport rates were measured over a 29- to 64-hour, generally 48-hour, period, under both dry (10 ml CDES alone) and wet (8 ml CDES+2 ml water) conditions. The test cells were the same as those described for Exs. 9 and 10. The liquid (CDES and, if present, water) was placed on the top side of the film. Air was blown through the compartment adjacent the bottom side of the film at a rate of 4 l/min and then into a glass tube packed with 150 mg of coconut shell charcoal adsorbent. The material collected on the adsorbent was desorbed by placing the latter in carbon disulfide and agitating it, and the carbon disulfide extract was analyzed by gas chromatography. The results are summarized in Table VII.

TABLE VII

| | Metal | Transport Rate of CDES ($g/m^2 \cdot 24$ hr) | |
|---|---|---|---|
| Ex. | Ion | Dry | Wet |
| 21 | $Ca^{+2}$ | 0.017* | ND |
| 22 | $Mg^{+2}$ | 0.072 | 0.016* |
| R | $H^{+}$ | 0.0 | 1.14 |
| S | $Na^{+}$ | ND** | 0.081 |
| T | $K^{+}$ | ND | ND |

*upper limit; actual value may be lower.
**ND means "not detectable"

Industrial Applicability

Composite fabrics containing a continuous film of a highly fluorinated ion exchange polymer as defined herein are useful in protective garments such as jackets, trousers, complete suits hermetically sealed, gloves, boots, hats, head coverings, masks, etc. The garments are broadly useful for providing protection to workers in the chemical industry, firemen, forest fire fighters, race car drivers, crop dusters and airplane pilots, and they may have value for defensive use by military personnel. They are believed to provide protection against blistering agents which contain chloroethyl groups and toxic organophosphorus compounds by a dual action of preventing penetration by part of the substance, and of complexing with and/or detoxifying at least part of the substance which penetrates into the ion exchange barrier layer of the garment. The garments provided herein are technically advanced over those previously known in that they readily permit loss of perspiration and body heat while providing the needed protection. The garments are also waterproof in the sense that gross amounts of liquid will not penetrate the ion exchange film. The water entry pressure of the composite fabric is an order of magnitude above that of ordinary waterproof fabrics. Garments of the composite fabrics are virtually "watertight", yet "breathable". The composite fabrics can also be used for rain or water protection in any kind of rainwear, such as rainsuits, coats, parkas, ponchos, slickers, etc.

I claim:

1. A protective garment fabricated at least in part from a composite fabric, said fabric containing as the essential component thereof a continuous film of a highly fluorinated ion exchange polymer having sulfonic acid metal ion salt functional groups, said metal ion having a valence of 2, +3 or +4, there being at least one fluorine atom attached to each carbon atom to which each said functional group is attached, said polymer having an equivalent weight no greater than about 2000.

2. The protective garment of claim 1 wherein said polymer is a perfluorinated polymer.

3. The protective garment of claim 2 wherein said metal ion selected from the group consisting of $Ca^{+2}$, $Mg^{+2}$, $Al^{+3}$, $Zn^{+2}$, $Ce^{+3}$, $Ce^{+4}$, $Cr^{+3}$, $Ni^{+2}$ and $Co^{+2}$.

4. The protective garment of claim 3 wherein said metal ion is $Ca^{+2}$.

5. The protective garment of claim 2 or 4 wherein said polymer has an equivalent weight no greater than about 1500, and the thickness of said film is in the range of about 2.5 to 125 micrometers.

6. The protective garment of claim 5 wherein the thickness of said film is in the range of about 10 to 50 micrometers.

7. The protective garment of claim 1 wherein said composite fabric further comprises a microporous polyolefin cloth.

8. The protective garment of claim 7 wherein said polyolefin is polytetrafluoroethylene or polypropylene.

9. The protective garment of claim 1 wherein said composite fabric further comprises a component fabric of fibers of poly-meta-phenylene isophthalamide or poly-para-phenylene terephthalamide or a blend thereof.

10. The protective garment of claim 1 wherein said composite fabric further comprises a component fabric of fibers of polyhexamethylene adipamide, polyhexamethylene decanedicarboxamide, polyhexamethylene dodecanedicarboxamide, polyepsilon-caproamide or the polyamide of bis-para-aminocyclohexylmethane and dodecanedicarboxylic acid.

11. The protective garment of claim 1, 4, 9 or 10 wherein said composite fabric consists of one layer of said continuous film and one layer of component fabric, and said garment is fabricated from said composite fabric so disposed that said film is toward the outside of said garment and said component fabric is toward the inside of said garment.

12. A waterproof protective cover as a tent or shelter fabricated at least in part from a composite fabric, said fabric containing as the essential component thereof a continuous film of a highly fluorinated ion exchange polymer having sulfonic acid metal ion salt functional groups, said metal ion having a valence of +2, +3, or +4, there being at least one fluorine atom attached to each carbon atom to which each said functional group is attached, said polymer having an equivalent weight no greater than about 2,000.

13. A waterproof protective cover as a tarpaulin fabricated at least in part from a composite fabric, said fabric containing as the essential component thereof a continuous film of a highly fluorinated ion exchange polymer having sulfonic acid metal ion salt functional groups, said metal ion having a valence of +2, +3, or +4, there being at least one fluorine atom attached to each carbon atom to which each said functional group is attached, said polymer having an equivalent weight no greater than about 2,000.

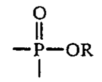

14. A process wherein (a) water permeates from a first space adjacent a first side of a barrier to a second space adjacent the second side of said barrier, said barrier having as the essential component thereof a continuous film of a highly fluorinted ion exchange polymer having sulfonic acid metal ion salt functional groups, said metal ion havinga valence of +2, +3 or +4, there being at least one fluorine atom attached to each carbon atom to which each said sulfonic acid group is attached, said polymer having an equivalent weight no greater than about 2000, and (b) a hazardous substance, said substance being a toxic organophosphorus compound having a